United States Patent [19]

Grosse-Bley et al.

[11] Patent Number: 5,357,001
[45] Date of Patent: Oct. 18, 1994

[54] OPTICALLY ACTIVE AMINO ACID SULPHOXIDE AND AMINO ACID SULPHONE DERIVATIVES, THEIR PREPARATION, THEIR POLYMERISATION AND USE AS ADSORBENTS FOR CHROMATOGRAPHIC RESOLUTION OF RACEMATES

[75] Inventors: Michael Grosse-Bley, Köln; Bruno Börner, Bergisch Gladbach; Rolf Grosser, Leverkusen; Walter Lange, Köln; Franz-Peter Hoever, Köln; Dieter Arlt, Köln, all of Fed. Rep. of Germany

[73] Assignee: Bayer Aktiengesellschaft, Leverkusen, Fed. Rep. of Germany

[21] Appl. No.: 81,537

[22] Filed: Jun. 23, 1993

[30] Foreign Application Priority Data

Jul. 2, 1992 [DE] Fed. Rep. of Germany ....... 4221711

[51] Int. Cl.$^5$ .......................... C08F 8/34; C08F 20/58; C08F 20/60; C08F 28/00
[52] U.S. Cl. .................. 525/326.1; 525/326.2; 525/326.7; 525/328.5; 525/330.3; 525/330.4; 525/330.5; 526/194; 526/199; 526/238.1; 526/243; 526/258; 526/288; 526/304; 526/305; 210/656; 210/660; 436/8; 436/106; 436/119; 536/122
[58] Field of Search ............... 526/238.1, 243, 245, 526/248, 249, 288, 304, 199, 220, 258, 166, 194; 525/328.2, 328.5, 330.7, 326.1, 326.3, 326.7, 330.4, 330.5, 330.3; 210/656

[56] References Cited

U.S. PATENT DOCUMENTS 3,615,624 10/1971 Smith et al. ................. 430/627
3,846,306 11/1974 Barker et al. ................ 257/497
3,884,761 5/1975 Cowling .................... 435/180
4,696,980 9/1987 Porath ..................... 525/326.1
4,914,159 4/1990 Bomer et al. ............... 525/328.2
4,937,000 6/1990 Bomer et al. ............... 210/656
5,274,167 12/1993 Lange et al. ............... 526/304

FOREIGN PATENT DOCUMENTS 0379917 1/1990 European Pat. Off. .
0379917 8/1990 European Pat. Off. .
0464488 1/1992 European Pat. Off. .
0520242 12/1992 European Pat. Off. .

*Primary Examiner*—Paul R. Michl
*Assistant Examiner*—Tae H. Yoon
*Attorney, Agent, or Firm*—Sprung Horn Kramer & Woods

[57] ABSTRACT

The invention relates to new optically active amino acid derivatives of the general formula (I)

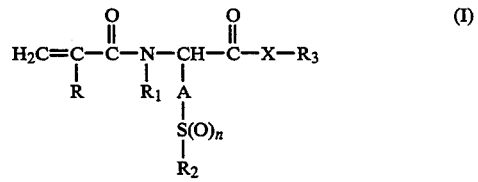

in which n, R, $R_1$, $R_2$, $R_3$, X and A have the meaning given in the description, which amino acid derivatives contain sulphoxide or sulphone groups, to two basic synthetic routes for the preparation from sulphur-containing amino acids, to the polymerization of these monomers and to the use of the polymers as optically active adsorbents for chromatographic resolution of racemates to give the enantiomers.

9 Claims, No Drawings

OPTICALLY ACTIVE AMINO ACID SULPHOXIDE AND AMINO ACID SULPHONE DERIVATIVES, THEIR PREPARATION, THEIR POLYMERISATION AND USE AS ADSORBENTS FOR CHROMATOGRAPHIC RESOLUTION OF RACEMATES

The invention relates to new optically active amino acid derivatives containing sulphoxide or sulphone groups, to two basic synthetic routes for their preparation from sulphur-containing amino acids, to the polymerisation of these monomers and to the use of the polymers as optically active adsorbents for chromatographic resolution of racemates to give the enantiomers.

Resolution of biologically active racemates to give the enantiomers has recently gained more and more importance because it was found that the enantiomers of a racemate usually differ considerably in activity and side effects. Accordingly, in most cases, there is a great interest in pharmacology or toxicology in having sufficient amounts of both enantiomers of a chirally active substance available even at the very early development stage of, for example, a new pharmaceutical substance. Chromatographic resolution of racemates can often provide sufficient amounts of both enantiomers for further biological tests (also increasingly in crop protection) easily and within a short period of time at an early stage at which enantioselective synthesis is frequently not yet available and conventional resolution of racemates via diastereomeric salts proceeds only in poor yields.

A wide range of adsorbents for chromatographic resolution of racemates have already been proposed. Adsorbents which so far have proven useful are the polymeric (meth)acrylic acid derivatives of optically active amino compounds described, for example, in EP-A 379,917, if appropriate in a form immobilised on inorganic supports.

Surprisingly, it has now been found that optically active sulphoxides and sulphones (hereinafter called S-oxides) of sulphur-containing amino acid derivatives containing a polymerisable group lead to very interesting new optically active chromatographic adsorbents which in a series of racemates give significantly improved resolution results compared with known resolution materials, in particular sulphur-free or S-oxide-free amino acid derivatives.

Accordingly, the invention relates to optically active amino acid derivatives containing S-oxides and having the formula (I)

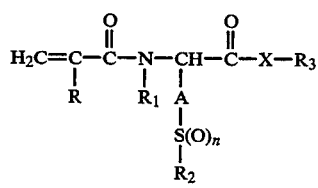

in which
n has the value 1 or 2,
R represents hydrogen, methyl or fluorine,
$R_1$ represents hydrogen or $C_1$-$C_4$-alkyl or together with $R_2$ forms a methylene group or a dimethylene group, each of which can be mono- or disubstituted by $C_1$-$C_4$-alkyl,
$R_2$ represents a straight-chain, branched or cyclic alkyl radical having up to 10 C atoms, $C_6$-$C_{14}$-aryl,

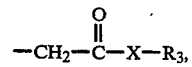

$C_2$-$C_{10}$-acyl, substituted or unsubstituted benzoyl or benzyl or together with $R_1$ forms a bridge described there,
$R_3$ represents a straight-chain, branched or cyclic alkyl radical having up to 20 C atoms which is unsubstituted or mono- to trisubstituted by halogen, alkoxy having 1 to 4 C atoms, aralkoxy having 7 to 16 C atoms or aryl having 6 to 10 C atoms,
X denotes oxygen or an $NR_4$ group in which $R_4$ represents hydrogen or $C_1$-$C_4$-alkyl or together with $R_3$ forms a nitrogen-containing 5- to 7-membered ring which may be mono- or disubstituted by $C_1$-$C_4$-alkyl- or $C_1$-$C_6$-alkoxycarbonyl,
A represents a methylene or dimethylene group which is unsubstituted or mono- or disubstituted by $C_1$-$C_4$-alkyl.

Preferred compounds of the formula (I) are those in which
n has the value 1 or 2,
R represents hydrogen, methyl or fluorine,
$R_1$ denotes hydrogen or methyl or together with $R_2$ forms a methylene group, which can be mono- or disubstituted by methyl or monosubstituted by tertiary-butyl, or a dimethylene group,
$R_2$ represents alkyl having up to 8 C atoms, phenyl, benzyl, benzoyl and,

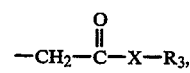

or together with $R_1$ forms a bridge described there,
$R_3$ represents a $C_{10}$-terpenyl radical, an adamantyl radical, a decahydronaphthyl radical, a 1-phenylethyl radical, a $C_5$-$C_{12}$-cycloalkyl radical, such as cyclopentyl, cyclohexyl or cycloheptyl, or a branched $C_3$-$C_{12}$-alkyl radical, such as isopropyl, 3-pentyl or 5-heptyl,
X denotes oxygen or an $NR_4$ group in which $R_4$ represents hydrogen or $C_1$-$C_4$-alkyl or together with $R_3$ forms a nitrogen-containing 5- to 7-membered ring which may be unsubstituted or mono- or disubstituted by $C_1$-$C_4$-alkyl- or $C_1$-$C_6$-alkoxycarbonyl,
A represents a methylene, dimethylmethylene or dimethylene unit.

The optically active amino acid derivatives are preferably derived from optically active sulphur-containing amino acids, such as, for example, cysteine, penicillamine or homocysteine. Of particular interest for this purpose are compounds whose SH function is alkylated, such as, for example, in S-methyl-cysteine, S-benzyl-cysteine, S-methyl-penicillamine, methionine, ethionine or butionine, or acylated, such as, for example, in S-acetyl-cysteine, or alkoxycarbonylmethylated such as, for example, in S-menthoxycarbonylmethyl-cysteine, or is linked to the amino group via an alkylene bridge, such as, for example, in thioproline, 2,2-dimethyl-thioproline, 5,5-dimethylthioproline or 2-tert.-butylthioproline.

For R₃, the use of optically active radicals is particularly advantageous, for example of the 1-phenylethyl, 1-(1-naphthylethyl), 1-(2-naphthylethyl), of the d- or l-menthyl, d- or l-neomenthyl, d- or l-bornyl, d- or l-fenchyl, of the d- or l-pinanyl radical or of the 3-methylenylpinanyl radical.

The optically active S-oxide-containing amino acid derivatives according to the invention of the formula (I) can be prepared by reaction of optically active amino acid S-oxides of the formula (II)

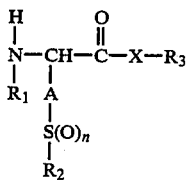

in which n, $R_1$, $R_2$, $R_3$, A and X have the meaning given under formula (I), or acid addition products thereof with acryloyl derivatives of the formula (III)

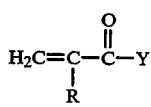

in which

R has the meaning given under the formula (I) and

Y represents fluorine, chlorine or bromine or the radical

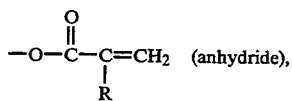

if appropriate in the presence of an acid-binding agent in inert organic solvents.

Suitable acid addition compounds of the amino acid S-oxides to be used as starting materials are salts of these amino acid S-oxides with inorganic or organic acids. Preference is given to mineral acids, such as hydrochloric acid, hydrobromic acid, sulphuric acid, phosphoric acid, or organic acids, such as acetic acid, trifluoroacetic acid, methane-, ethane-, benzene- or toluenesulphonic acid.

Suitable solvents are any organic solvents which are inert under the reaction conditions. Preference is given to hydrocarbons, such as toluene, petroleum ether, or halogenated hydrocarbons, such as dichloromethane, dichloroethane or trichloroethylene, or ethers, such as tert.-butyl methyl ether.

Suitable acid-binding agents are in particular the customary inorganic or organic bases; the preferably used bases are alkali metal hydroxides or alkaline earth metal hydroxides, such as sodium hydroxide, potassium hydroxide, lithium hydroxide, calcium hydroxide or barium hydroxide, alkali metal carbonates or alkaline earth metal carbonates, such as sodium carbonate or potassium carbonate or sodium bicarbonate, alkali metal alkoxides, such as sodium methoxide, sodium ethoxide, potassium methoxide, potassium ethoxide, potassium tert.-butoxide, or amines, such as triethylamine or pyridine.

Reaction of the acryloyl derivatives of the formula (III) with the S-oxides of the formula (II) is preferably carried out at temperatures of −78° to +100° C., in particular of −20° to +60° C.

The optically active amino acid S-oxides of the formula (II) used as starting compounds can be prepared by processes known per se.

If, in the case of the sulphoxides (n=1 in formula (II)), it is desired to obtain the diastereomerically and enantiomerically pure compounds of the formula (II), oxidation of the sulphur is advantageously carried out at the stage of the free, sulphur-containing amino acid, using, for example, hydrogen peroxide. The mixture of diastereomers (new asymmetric centre on sulphur) formed in this case can be resolved by the difference in solubility of diastereomeric salts.

Oxidation of the free amino acid L-methionine to the sulphoxide, followed by resolution of the 1:1 mixture of diastereomers via the difference in solubility of the picrates in water is known. The diastereomer with (S)-configuration on the sulphur can be obtained from the sparingly solvent picrate and the diastereomer with (R) configuration on the sulphur from the soluble picrate by releasing it using n-pentylamine.

The further route is via known processes of peptide chemistry, such as introduction of an N-protecting group (for example tert.-butoxycarbonyl), preparation of the ester or amide by coupling with the corresponding alcohols or amines (dicyclohexylcarbodiimide method or activation by mixed anhydride using chloroformic ester) and elimination of the N-protecting group to give compounds of the formula (II).

The sulphones (n=2 in formula (II) ) can basically also be prepared by the synthetic route described above. Here, of course, resolution of the diastereomers at the beginning is omitted.

In a second, alternative synthetic route, oxidation of the sulphur is not carried out until the last step takes place. This method is suitable in particular for sulphones (n=2 in formula (I)) and 1:1 mixtures of diastereomers of sulphoxides (n=1 in formula (I)). The optically active S-oxides-containing amino acid derivatives according to the invention of the formula (I) are in this case obtained by oxidation of optically active sulphur-containing amino acid derivatives of the formula (IV)

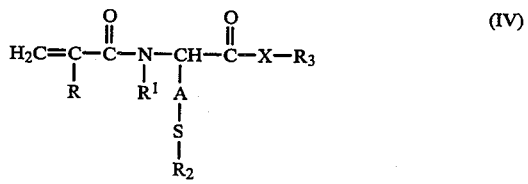

in which

R, $R_1$, $R_2$, $R_3$, A and X have the meaning given under formula (I), with oxidising agents, such as hydrogen peroxide, sodium metaperiodate, 3-chloroperbenzoic acid, magnesium monoperoxyphthalic acid, the triple salt of Caro's acid ($KHSO_5 \times KHSO_4 \times K_2SO_4$) and other oxygen carriers which are suitable to convert thioethers into sulphoxides and sulphones.

Suitable solvents are in particular alcohols, such as methanol and ethanol, acetic acid, water and methylene chloride and mixtures of these solvents.

Oxidation of the sulphur-containing amino acid derivatives of the formula (IV) is preferably carried out at temperatures of −78° C. to +100° C., particularly preferably −20° C. to +60° C.

Preferably, 1 to 1.5 equivalents of oxidising agent are used for preparing the sulphoxide (n=1, formula (I)) and 2 to 3 equivalents of oxidising agent are used for preparing the sulphone (n=2, formula (I)) in each case from the sulphur-containing amino acid derivatives of the formula (IV).

The optically active sulphur-containing amino acid derivatives of the formula (IV) used as starting compounds can be prepared by methods known per se from peptide chemistry (cf. route to (I) via (II) but in each case n=0 ).

An abbreviated process for obtaining the starting materials of the formula (IV) which omits the protective group chemistry uses the direct reaction of the free amino acid in basic medium with the corresponding acryloyl derivatives of the formula (III) and the coupling of the N-acryloylated amino acids with the corresponding amines or alcohols ($R_3$—X—H) using ethyl 1,2-dihydro-2-ethoxyquinoline-1-carboxylate (EEDQ method) or N,N′-dicyclohexylcarbodiimide (DCC method).

The invention also relates to the optically active polymers and copolymers obtainable by polymerisation or copolymerisation of the optically active acryloylamino acid S-oxide derivatives of the formula (I) which polymers and copolymers contain at least 40 mol %, preferably at least 50 mol %, of structural units of the formula (V),

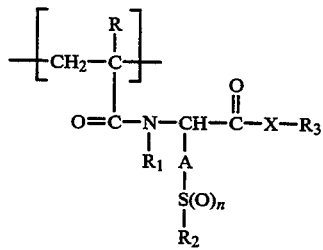

(V)

in which n, R, $R_1$, $R_2$, $R_3$, A and X have the meaning given under formula (I).

The optically active polymers according to the invention of the formula (V) are preferably in the form of crosslinked insoluble but swellable bead polymers or in a form bound to finely divided inorganic support materials, such as, for example, silica gel. They can also be prepared as linear polymers which are soluble in suitable organic solvents. Furthermore, it is possible to copolymerise various sulphur-containing acryloylamino acid S-oxide derivatives according to the invention of the formula (I) and to incorporate in the polymers 0.1 to 60, preferably 0.1 to 20 mol % of copolymerisable other monomers.

The crosslinked polymers are preferably present in the form of small particles (beads) having a particle diameter of 5 to 200 μm. They are prepared, for example, by suspension polymerisation of the optically active sulphur-containing acryloylamino acid S-oxide derivatives of the formula (I) with 0.5 to 50 mol %, preferably 1 to 30 mol %, particularly preferably 3 to 20 mol %, (relative to the total amount [mol] of the monomers used) of a suitable crosslinking agent in a manner known per se.

The degree of swelling of the (bead) polymers can be adjusted by the type and amount of the crosslinking agents and the solvent using customary methods.

In practical application, (bead) polymers having a degree of swelling (DS) of 1.1 to 12.0, preferably 2.0 to 6.0, have proven suitable.

The degree of swelling DS is determined as follows:

$$DS = \frac{\text{Polymerisation volume (swollen)}}{\text{Polymerisation volume (unswollen)}}$$

Suitable crosslinking agents are compounds containing at least two polymerisable vinyl groups. Preferred crosslinking agents are alkanediol diacrylates, such as 1,6-hexanediol diacrylate, 1,4-butanediol diacrylate, 1,3-propanediol diacrylate or 1,2-ethylene glycol diacrylate, or alkanediol dimethacrylates, such as 1,4-, 1,3- or 2,3-butanediol dimethacrylate, 1,3-propanediol dimethacrylate or 1,2-ethylene glycol dimethacrylate, aromatic divinyl compounds, such as, for example, divinylbenzene, divinylchlorobenzene or divinyltoluene, divinyl dicarboxylates, such as divinyl adipate, divinyl benzenedicarboxylates, divinyl terephthalates, N,N′-alkylenediacrylamides, such as N,N′-methylenediacrylamide, N,N′-ethylenediacrylamide, N,N′-methylenedimethacrylamide, N,N′-ethylenedimethacrylamide or N,N′-dimethyl-ethylenediacrylamide. N,N′,N″-tris(acryloyl)-1,3,5-perhydrotriazine or N,N′,N″-bis(acryloyl)piperazine can also be used.

Suitable free radical formers are the customary free radical formers. Preference is given to peroxides, such as, for example dibenzoyl peroxide, dilauroyl peroxide or di-ortho-toluoyl peroxide, peresters, such as tert.-butyl perpivalate or tert.-butyl peroctanoate, or azo compounds, such as, for example, azobisisobutyronitrile (AIBN). Mixtures of various free radical formers can also be used.

The polymerisation components are dissolved in a water-immiscible organic solvent, preferably an aliphatic or aromatic hydrocarbon, such as hexane, heptane, isodecane, benzene or toluene, a halogenated hydrocarbon, such as di-, tri-, tetrachloromethane or 1,2-dichloroethane, an ester, such as ethyl acetate, butyl acetate or dialkylcarbonate, or a water-insoluble ketone, such as methyl isobutyl ketone or cyclohexanone.

The organic phase is uniformly distributed in the aqueous solution of a protective colloid, preferably in aqueous solution of polyvinyl alcohol, polyvinylpyrrolidone or of a methacrylic acid/methyl methacrylate copolymer by means of an effective stirrer. Approximately 1 to 20, preferably 2 to 10, parts by weight of aqueous phase are used per part by weight of organic phase. The polymerisation mixture is heated in an inert gas atmosphere, preferably under nitrogen, to temperatures of 30° C. to 100° C., preferably 40° C. to 80° C., with stirring. The polymerisation time is 2 to 24, preferably 4 to 12 hours. The copolymer obtained in this manner is separated from the liquid phase by filtration, purified by thorough washing with water and with organic solvents, such as methanol, ethanol, benzene, toluene, di-, trichloromethane or acetone and then dried.

In particular for analytical applications, the optically active polymers according to the invention are preferably used in a form bound to finely divided inorganic supports. Such optically active chromatographic phases can be prepared, for example, by the process described in DE-A 3,706,890.

Preference is given to polymerisation of the optically active sulphur-containing amino acid S-oxide derivatives of the formula (I) in the presence of silica gel/vinyl phases obtainable by known methods, or of silica gel/diol phases esterified with (meth)acrylic acid. This polymerisation can take place in the absence of solvents or in the presence of solvents or of precipitants for the poly-N-acryloylamide S-oxide derivatives. The free radical formers used for preparing the bead polymers can also be used as initiators.

Polymer-modified silica gels preferably contain 1 to 40% by weight, in particular 5 to 30% by weight, of optically active monomer (I) relative to the total weight. They are thoroughly washed with solvents for the polymer and dried in vacuo.

Here, it is of course also possible to use mixtures of two or more of the N-acryoylamino acid S-oxide derivatives, if appropriate also in combination with further copolymerisable monomers.

The invention furthermore relates to the use of the polyacrylamide S-oxides according to the invention as such or in crosslinked form or in a form bound to silica gel for the chromatographic resolution of racemic mixtures to give the optical antipodes. The polymers according to the invention have proven particularly suitable for the chromatographic resolution of hexahydrocarbazole derivatives, such as, for example, 3-r-(4-fluorophenylsulphonamido)-9-(2-carboxyethyl)-1,2,3,4,4a,9a-hexahdrocarbazole, benzodiazepines, such as oxazepam, arylpropionamides, such as ketoprofen- and ibuprofenamide, dihydropyridines, such as, for example, 5-methyl 1,4-dihydro-2,6-dimethyl-4-(2-trifluoromethylphenyl)pyridine-3,5-dicarboxylate, binaphthol, benzoin and hydrobenzoin, stilbene oxide, chlorothalidone, thiaprofenic acid and mandelamide.

Depending on the type and property of the racemate to be resolved, the composition of the eluent can be selected and optimised in the usual manner. For chromatographic resolution of racemates, the polyacrylamide S-oxides according to the invention which are bound to the silica gel can be used under HPLC conditions.

The racemate resolution capacity of the polymers is expressed by the capacity ratios ($k'_{1(2)}$ values) for the two enantiomers (1) and (2) and the resulting enantioselectivity value $\alpha$. These chromatographic parameters are defined as follows:

$$\text{Capacity ratio } k'_{1(2)} = \frac{t_{1(2)} - t_0}{t_0}$$

$$\text{Enantioselectivity } \alpha = \frac{k'_2}{k'_1}$$

$t_0$ = Dead time of the column
$t_{1(2)}$ = Retention time of enantiomer 1 eluted first and enantiomer 2 eluted later Preparative resolution of racemic mixtures to give their optical antipodes using the polymers according to the invention is preferably carried out by column chromatography. Particularly advantageously, chromatographic resolution is carried out using bead polymers having a specified particle size distribution; good separation efficiencies are obtained with bead polymers having a particle size distribution of 5 to 200 μm, preferably 15 to 100 μm.

The operating methodology of resolution by column chromatography is known. The polymer is usually suspended in the eluent, and the suspension is poured into a glass column. After the eluent has run off, the racemate to be resolved is applied to the column as a solution in the eluent. The product is then eluted using eluent, and the enantiomers in the eluate are detected by photometry and/or polarimetry by means of suitable flow cells.

The eluents used are usually organic solvents or solvent mixtures which swell the polymer used as adsorbent and dissolve the racemate to be resolved. Examples are: hydrocarbons, such as benzene, toluene or xylene, ethers, such as diethyl ether, tert.-butyl methyl ether, dioxane or tetrahydrofuran, halogenated hydrocarbons, such as di-or trichloromethane, acetone, acetonitrile or ethyl acetate, alcohols, such as methanol, ethanol, n-propanol, isopropanol or n-butanol, or else mixtures of the solvents mentioned. Mixtures of toluene with tetrahydrofuran, dioxane or isopropanol have proven to be particularly suitable.

EXAMPLES

1) Preparation of the Optically Active S-oxides-containing Amino Acid Derivatives of the Formula (I) from (II) and (III)

Example 1 a) (S)-L-Methionine sulphoxide and (R)-L-methionine sulphoxide

Preparation and resolution of the diastereomeric sulphoxides of L-methionine via the picrates by the procedure of J. Biol. Chem. 169 (1947) 477.

b) (S)-N-BOC-L-Methionine sulphoxide 0.1 mol of $NaHCO_3$ and 100 ml of 1N sodium hydroxide solution are added to 0.1 mol of (S)-L-methionine sulphoxide in 300 ml of dioxane:water=2:1 at 5° C. 0.11 mol of $(BOC)_2O$ is added, the mixture is allowed to warm to room temperature and stirring is continued for another 30 minutes. The dioxane is distilled off in a rotary evaporator, the aqueous phase is cooled with ice, covered with a layer of ethyl acetate and brought to a pH of 2–3 by means of 4N $KHSO_4$ solution. It is saturated with common salt and extracted two more times with ethyl acetate. The organic phase is dried with $MgSO_4$ and concentrated.

Yield: 13.8 g≙52%
$[\alpha]_D$: +91.8° (C=1, $H_2O$).

c) (S)-N-BOC-L-Methionine-1-menthylamide sulphoxide 50 mmol of $NEt_3$ are added to 50 mmol of (S)-N-BOC-L-methionine sulphoxide at 0° C. in 125 ml of absolute THF. 50 mmol of ethyl chloroformate are then added dropwise at −12° C. After 15 minutes, 50 mmol of L-menthylamine are added. Stirring at 0° C. is continued for 30 minutes, and the mixture is then allowed to warm to room temperature. It is concentrated, taken up in $CH_2Cl_2$, washed with 1N hydrochloric acid, dried over $MgSO_4$ and concentrated again.

Yield: 20 g≙100% d) (S)-L-Methionine-1-menthylamide sulphoxide 100 ml of freshly distilled trifluoroacetic acid are added dropwise to 50 mmol of (S)-N-BOC-L-methionine-1-menthylamide sulphoxide in 100 ml of $CH_2Cl_2$ at 0° C. The mixture is allowed to warm to room temperature and additionally stirred for 1 hour. It is concentrated at room temperature, taken up again in 200 ml of $CH_2Cl_2$ and brought to a pH of 12 with 15% strength NaOH at 0° C. with stirring. The organic phase is rapidly separated off, and the aqueous phase is extracted two more times with $CH_2Cl_2$. The combined organic phases are back-extracted once with water, dried over $MgSO_4$ and concentrated.

Yield: 15 g≙100% e) (S)-N-Methacryloyl-N-methionine-1-menthylamide sulphoxide 50 mmol of $NEt_3$ are added to 50 mmol of (S)-N-methacryloyl-N-methionine-1-menthylamide sulphoxide in 40 ml of $CH_2Cl_2$ at 0° C. 50 mmol of freshly distilled methacryloyl chloride in 30 ml of $CH_2Cl_2$ are added dropwise at −20° C. The mixture is allowed to warm to room temperature, washed with water, 1N hydrochloric acid and unsaturated $NaHCO_3$ solution, dried over $MgSO_4$ and concentrated. The solid is purified by flash chromatography on 300 g of silica gel using $CH_2Cl_2$:MeOH=97:3 as eluent.

Yield: 9 g≙50%
M.p.: 174° C.
$[α]_D$: −20.3° (c=1, $CHCl_3$).

2) Preparation of the Optically Active S-oxide-containing Amino Acid Derivatives of the Formula (I) by Oxidation of Optically Active Sulphur-containing Amino Acid Derivatives of the Formula (IV)

EXAMPLE 3 a) L-Methionine-1-menthyl ester 0.3 mol of L-methionine, 0.39 mol of (−)-menthol and 0.33 mol of p-toluenesulphonic acid monohydrate are heated in 1.2 l of toluene using a water separator. The bath temperature should not exceed 140° C. After 30 hours, a clear solution has been formed and 10 ml of water have been separated off (theory: 11.4 ml).

After cooling, the mixture is brought to a pH of 11 to 12 with 15% strength sodium hydroxide solution, the toluene phase is separated off, and the aqueous phase is extracted two more times with toluene. The combined toluene phases are washed once with water, dried over magnesium sulphate and concentrated. Excess (−)-menthol is distilled off from the crude product under reduced pressure.

Yield (distillation residue): 71 g≙82%
$[α]_D$: −38.1° (c=1, $CHCl_3$).

b) N-Methacryloyl-L-methionine 1-menthyl ester 66 mmol of triethylamine are added to 60 mmol of L-methionine 1-menthyl ester in 500 ml of dry dichloromethane at 0° C. The mixture is cooled to −10° C., and 65 mmol of freshly distilled methacryloyl chloride in 50 ml of dichloromethane are added dropwise. The mixture is allowed to warm to room temperature and additionally stirred for 1 hour. It is washed with water, 1N hydrochloric acid and saturated sodium bicarbonate solution, dried over magnesium sulphate and concentrated. The crude product is recrystallised from n-heptane.

Yield: 17.3 g≙81%
M.p.: 80°–82° C.
$[α]_D$: −27.3° (c=1, $CHCl_3$).

c) N-Methacryloyl-L-methionine 1-menthyl ester (R,S)-sulphoxide 20 mmol of N-methacryloyl-L-methionine 1-menthyl ester in 40 ml of methanol are added dropwise to 42 ml of a 0.5M solution of sodium metaperiodate in water at 0° C. After 6 hours, precipitated sodium iodate is filtered off with suction. The filtrate is extracted several times with chloroform. The organic phase is dried over magnesium sulphate and concentrated. The crude product crystallises completely and is recrystallised from n-heptane.

Yield: 6 g≙81%
M.p.: 79° C.
$[α]_D$: 33.4° (c=1, $CHCl_3$).
$^1H$ NMR ($CDCl_3$): shows 2 diastereomers in the ratio of 1:1

EXAMPLE 4

N-Methacryloyl-L-methionine 1-menthyl ester sulphone 2.4 Equivalents of 35% strength hydrogen peroxide are added to 15 mmol of N-methacryloyl-L-methionine 1-menthyl ester (see Example 3b)) in 60 ml of glacial acetic acid. The mixture is additionally stirred at 50° C. for 8 hours. The reaction solution is concentrated at room temperature. The crude product is recrystallised from n-heptane.

Yield: 5.35 g≙92%
M.p.: 141° C.
$[α]_D$: −18.6° (c=1, $CHCl_3$).

EXAMPLE 5 a) N-BOC-L-Methionine-1-menthylamide 0.45 mol of triethylamine is added to 0.45 mol of N-BOC-L-methionine in 1 l of THF at 0° C. The mixture is cooled to −12° C., and 0.45 mol of ethyl chloroformate is added dropwise. Stirring at −12° C. is continued for 20 minutes, and 0.45 mol of L-menthylamine is added dropwise. Stirring at 0° C. is continued for 45 minutes, and the mixture is then allowed to warm to room temperature.

The THF is distilled off; the residue is taken up in 1 l of dichloromethane, and the solution is washed with water and 1N hydrochloric acid, dried over magnesium sulphate and concentrated again.

Crude yield: 170 g=98%
(contains about 14% of N-menthyl-ethylurethane by GC).

b) L-Methionine-1-menthylamide 300 ml of trifluoroacetic acid are added to 0.4 mol of N-BOC-L-methionine-1-menthylamide in 300 ml of dichloromethane at 0° C. The mixture is allowed to warm to room temperature and additionally stirred for 1 hour. The solution is concentrated and again taken up in 500 ml of dichloromethane. It is brought to a pH of 12 with 15% strength sodium hydroxide solution with cooling. The organic phase is separated off. The aqueous phase is extracted two more times with dichloromethane. The combined organic phases are washed with water, dried over magnesium sulphate and concentrated.

Crude yield: 102 g=89% (still contains urethane, see above)

c) N-Methacryloyl-L-methionine-1-menthylamide 134 mmol of triethylamine are added to 134 mmol of L-methionine-1-menthylamide in 1.2 l of dichloromethane at 0° C. After cooling to −10° C., 134 mmol of freshly distilled methacryloyl chloride are added dropwise. The mixture is allowed to warm to room temperature and washed with water, 1N hydrochloric acid and saturated sodium bicarbonate solution. After drying over magnesium sulphate, the solvent is distilled off.

The crystalline crude product is recrystallised from n-heptane.

Yield: 37.3 g ≙ 79%
M.p.: 161°-163° C.
$[\alpha]_D$: −63.4° (c=1, CHCl$_3$).

d) N-Methacryloyl-L-methionine-1-menthylamide (R,S)-sulphoxide 1.2 Equivalents of 35% strength hydrogen peroxide are added to 19 mmol of N-methacryloyl-L-methionine-1-menthylamide in 50 ml of ethanol at room temperature. Stirring is continued for 18 hours. The reaction solution is concentrated at room temperature. The crude product is crystallised from tert.-butyl methyl ether.

Yield: 5.9 g ≙ 84%
M.p.: 155°-158° C.
$[\alpha]_D$: −67.4° (c=1, CHCl$_3$).
$^1$H NMR (CDCl$_3$): shows 2 diastereomers in the ratio of 1:1

EXAMPLE 6

N-Methacryloyl-L-methionine-1-menthylamide sulphone 2.4 Equivalents of 35% strength hydrogen peroxide are added to 15 mmol of N-methacryloyl-L-methionine-1-menthylamide (see Example 5c)) in 75 ml of glacial acetic acid, and stirring at 50° C. is continued for 18 hours. After concentrating at room temperature, the product is crystallised from tert.-butyl methyl ether.

Yield: 2.25 g ≙ 39%
M.p.: 156° C.
$[\alpha]_D$: −58.2° (c=1, CHCl$_3$).

EXAMPLE 7 a) N-Methacryloyl-S-methyl-L-cysteine 0.2 mol of S-methyl-L-cysteine is introduced into 100 ml of 2N sodium hydroxide solution at 0° C. 0.2 mol of freshly distilled methacryloyl chloride stabilised with hydroquinone and a further 100 ml of 2N sodium hydroxide solution are added dropwise in parallel in such a manner that T remains at 0° C. and the pH at 11. Stirring is continued for 1 hour. The mixture is brought to a pH of 2 with 85% strength ortho-phosphoric acid with vigorous stirring, saturated with solid sodium chloride and extracted with ethyl acetate. The extracts are dried with magnesium sulphate and concentrated (stabilised with hydroquinone).

Yield: 40 g ≙ 99%
$[\alpha]_D$: +29.3° (c=1, CHCl$_3$).

b) N-Methacryloyl-S-methyl-L-cysteine-1-menthylamide 0.2 mol of L-menthylamine in 300 ml of THF is added dropwise to 0.2 mol of N-methacryloyl-S-methyl-L-cysteine in 400 ml of THF at 5° C. 0.2 mol of EEDQ in 500 ml of THF is then added. Stirring at room temperature is continued for 4 days. The mixture is concentrated and taken up in 700 ml of ethyl acetate, washed 5 times with 1N hydrochloric acid, once with water, once with saturated common salt solution, dried over magnesium sulphate and concentrated. The crude product is crystallised from tert.-butyl methyl ether.

Yield: 40 g ≙ 58.5%
M.p.: 153° C.
$[\alpha]_D$: −81.4° (c=1, MeOH).

c) N-Methacryloyl-S-methyl-L-cysteine-1-menthylamide sulphone 120 mmol of N-methacryloyl-S-methyl-L-cysteine-1-menthylamide are suspended in 400 ml of acetone, 140 mmol of the triple salt of Caro's acid (2KHSO$_5$×KHSO$_4$×K$_2$SO$_4$) in 400 ml of water are added, and the mixture is stirred at 40° C. After the end of the reaction, excess peroxide is destroyed using 10% strength sodium bisulphite solution. Acetone is distilled off. The aqueous phase is extracted with ethyl acetate. The organic phase is dried over magnesium sulphate and concentrated.

Yield: 41.5 g ≙ 93%
M.p.: 199° C.
$[\alpha]_D$: −68.9° (c=1, CHCl$_3$).

EXAMPLE 8

N-Methacryloyl-S-methyl-L-cysteine-1-menthylamide (R,S)-sulphoxide 140 mmol of N-methacryloyl-S-methyl-L-cysteine-1-menthylamide (see Example 7b)) are introduced into 500 ml of glacial acetic acid. 1.2 Equivalents of 35% strength hydrogen peroxide are added dropwise at 15° to 20° C. After the end of the reaction, the mixture is concentrated at room temperature. The crude product is crystallised from tert.-butyl methyl ether.

Yield: 33 g ≙ 66%
M.p.: 194° C.
$[\alpha]_D$: −101.4° (c=1, CHCl$_3$).
$^1$H NMR (CDCl$_3$): shows 2 diastereomers in the ratio of 1:1.

EXAMPLES 24 and 25 a) (R)-Thioproline-1-menthyl ester 0.2 mol of (R)-thioproline, 0.256 mol of 1-menthol and 0.221 mol of p-toluenesulphonic acid monohydrate are refluxed in 1 l of toluene using a water separator until the theoretical amount of water has been separated off. The mixture is brought to a pH of 11-12 with 15% strength sodium hydroxide solution with cooling and extracted 3 times with toluene. The organic phase is washed once with water, dried over magnesium sulphate and concentrated. Excess 1-menthol is distilled off from the residue in vacuo.

Yield: 31 g ≙ 57%
$[\alpha]_D$: −129.0° (c=1, CHCl$_3$).

b) (R)-N-Acryloylthioproline 1-menthyl ester 0.1 mol of triethylamine is added to 0.1 mol of (R)-thioproline 1-menthyl ester in 800 ml of dichloromethane at 0° C. 0.1 mol of acryloyl chloride in 70 ml of dichloromethane are then added dropwise at −10° C. Stirring at room temperature is continued for 1 hour. The mixture is washed with water, 1N hydrochloric acid and saturated sodium bicarbonate solution, dried over magnesium sulphate and concentrated.

Yield: 31.5 g ≙ 97%
$[\alpha]_D$: −124.9° (c=1, CHCl$_3$).

c) (R)-N-acryloylthioproline 1-menthyl ester (R)-sulphoxide (Ex. 24c) and (S)-sulphoxide (Ex. 25c).

1.2 Equivalents of 35% strength hydrogen peroxide are added to 72 mmol of (R)-N-acryloylthioproline 1-menthyl ester in 200 ml of ethanol:glacial acetic acid=1:1. Stirring at room temperature is continued for 8 hours. The reaction solution is concentrated. The crude product which shows 2 distinguishable product spots in the TLC (tBuOMe:MeOH=95:5 as eluent) is chromatographed on silica gel using the eluents just mentioned.

Yield: 11.3 g ≙ 46% of the first fraction;
$[\alpha]_D$: −184.7° (c=1, CHCl$_3$)=Ex. 24c (R)-sulphoxide 3.0 g=12% of the second fraction; $[\alpha]_D$: −95.5° (c=1, CHCl$_3$)=Ex. 25c (S)-sulphoxide

TABLE 1

Synthesis of monomers

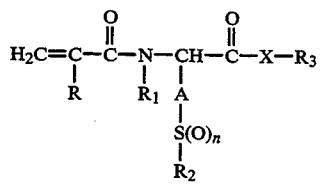

| Example | Radical groups | Product name | m.p. (°C.) | $[\alpha]_D$ (c = 1, CHCl$_3$) | Yield (%) |
|---|---|---|---|---|---|
| 1e | R = CH$_3$, R$_1$ = H, R$_2$ = CH$_3$<br>R$_3$ = l-menthyl,<br>X = NH, A = CH$_2$CH$_2$<br>n = 1 | N-methacryloyl-<br>L-methionine-<br>l-menthylamide<br>(S)-sulphoxide | 174 | −20.3 | 50 |
| 2 | As for 1e | N-Methacryloyl-<br>L-methionine-<br>l-menthylamide<br>(R)-sulphoxide | 151 | −75.0 | 58 |
| 3c | R = CH$_3$, R$_1$ = H, R$_2$ = CH$_3$<br>R$_3$ = l-menthyl, X = O<br>A = CH$_2$CH$_2$, n = 1 | N-Methacryloyl-<br>L-methionine-<br>l-menthyl ester<br>(R,S)-sulphoxide | 79 | −33.4 | 81 |
| 4 | As for 3c<br>but: n = 2 | N-Methacryloyl-<br>L-methionine-l-menthyl<br>ester sulphone | 141 | −18.6 | 92 |
| 5d | R = CH$_3$, R$_1$ = H, R$_2$ = CH$_3$<br>R$_3$ = l-menthyl, X = NH<br>A = CH$_2$CH$_2$, n = 1 | N-Methacryloyl-<br>L-methionine-<br>l-menthylamide<br>(R,S)-sulphoxide | 155–158 | −67.4 | 84 |
| 6 | As for 5d<br>but: n = 2 | N-Methacryloyl-<br>L-methionine-l-methyl-<br>amide (R)-sulphone | 156 | −58.2 | 39 |
| 7c | R = CH$_3$, R$_1$ = H, R$_2$ = CH$_3$<br>R$_3$ = l-menthyl, X = NH<br>A = CH$_2$, n = 2 | N-Methacryloyl-<br>S-methyl-L-cysteine-<br>l-menthylamide sulphone | 199 | −68.9 | 93 |
| 8 | As for 7c<br>but: n = 1 | N-Methacryloyl-S-methyl<br>L-cysteine-l-menthyl-<br>amide (R,S)-sulphoxide | 194 | −101.4 | 66 |
| 9 | R = H, R$_1$ = H, R$_2$ = CH$_3$<br>R$_3$ = l-menthyl, X = O<br>A = CH$_2$CH$_2$, n = 1 | N-Acryloyl-<br>L-methionine-<br>l-menthyl ester<br>(R,S)-sulphoxide | 90 | −23.1 | 62 |
| 10 | As for 9<br>but: X = NH | N-Acryloyl-<br>L-methionine-l-menthyl-<br>amide (R,S)-sulphoxide | 173 | −83.4 | 82 |
| 11 | As for 9<br>but: R$_3$ = d-menthyl | N-Acryloyl-<br>L-methionine<br>d-menthyl ester<br>(R,S)-sulphoxide | 82 | +62.0 | 84 |
| 12 | R = CH$_3$, R$_1$ = H, R$_2$ = CH$_3$<br>R$_3$ = d-menthyl, X = O<br>A = CH$_2$CH$_2$, n = 1 | N-Methacryloyl-<br>L-methionine<br>d-menthyl ester<br>(R,S)-sulphoxide | 61 | +48.6 | 66 |
| 13 | As for 12<br>but: X = NH | N-Methacryloyl-<br>L-methionine-<br>d-menthylamide<br>(R,S)-sulphoxide | 134 | +29.8 | 78 |
| 14 | R = H, R$_1$ = H, R$_2$ = CH$_3$<br>R$_3$ = d-methyl, X = NH<br>A = CH$_2$CH$_2$, n = 1 | N = Acryloyl-<br>L-methionine-<br>d-menthylamide<br>(R,S)-sulphoxide | 167 | +13.2 | 93 |
| 15 | As for 14<br>but: n = 2 | N-Acryloyl-<br>L-methionine-<br>d-menthylamide sulphone | 164 | +17.1 | 79 |
| 16 | R = H, R$_1$ = H, R$_2$ = CH$_3$<br>R$_3$ = l-menthyl, X = O<br>A = CH$_2$CH$_2$, n = 2 | N-Acryloyl-L-<br>methionine l-menthyl<br>ester sulphone | 140 | −11.0 | 95 |
| 17 | R = H, R$_1$ = H, R$_2$ = CH$_3$<br>R$_3$ = d-menthyl, X = O<br>A = CH$_2$CH$_2$, n = 2 | N-Acryloyl-L-<br>methionine d-menthyl<br>ester sulphone | 156 | +70.8 | 93 |
| 18 | R = H, R$_1$ = H, R$_2$ = CH$_3$<br>R$_3$ = l-menthyl, X = NH<br>A = CH$_2$CH$_2$, n = 2 | N-Acryloyl-L-<br>methionine-l-menthyl-<br>amide sulphone | 188 | −54.1 | 71 |
| 19 | R = CH$_3$, R$_1$ = H, R$_2$ = CH$_3$<br>R$_3$ = d-menthyl, X = NH<br>A = CH$_2$CH$_2$, n = 2 | N-Methacryloyl-<br>L-methionine-d-<br>menthylamide sulphone | 147 | +33.1 | 77 |
| 20 | R = CH$_3$, R$_1$ = H, R$_2$ = CH$_3$<br>R$_3$ = d-menthyl, X = O | N-Methacryloyl-<br>L-methionine | 110 | +32.7<br>(THF) | 80 |

TABLE 1-continued

Synthesis of monomers

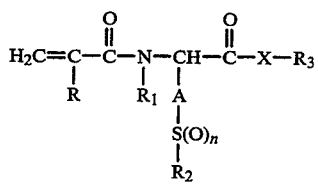

| Example | Radical groups | Product name | m.p. (°C.) | $[\alpha]_D$ (c = 1, CHCl$_3$) | Yield (%) |
|---|---|---|---|---|---|
| 21 | A = CH$_2$CH$_2$, n = 2<br>R = H, R$_2$R$_1$ = CH$_2$<br>R$_3$ = 1-menthyl, X = NH | d-menthyl ester sulphone (R)-N-Acryloyl thioproline-1-menthyl-amide (R)-sulphoxide | 100 | −244.8 | 71 |
| 22 | A = CH$_2$, n = 1<br>R = H, R$_2$R$_1$ = CH$_2$<br>R$_3$ = d-menthyl, X = O | (R)-N-Acryloyl thioproline d-menthyl ester (R)-sulphoxide | oil | −117.4 | 35 |
| 23 | A = CH$_2$, n = 1<br>R = H, R$_1$ = H, R$_2$ = CH$_3$<br>R$_3$ = Et, X = O | N-Acryloyl-L-methionine ethyl ester sulphone | 115 | +58.0 | 89 |
| 24c | A = CH$_2$CH$_2$, n = 2<br>R = H, R$_2$R$_1$ = CH$_2$<br>R$_3$ = 1-menthyl, X = 0 | (R)-N-Acryloyl thioproline 1-menthyl-ester (R)-sulphoxide | oil | −184.7 | 46 |
| 25c | A = CH$_2$, n = 1<br>As for 24 | (R)-N-Acryloyl thioproline 1-menthyl ester (S)-sulphoxide | oil | −95.5 | 12 |
| 26 | R = H, R$_2$R$_1$ = CH$_2$<br>R$_3$ = d-menthyl, X = NH<br>A = CH$_2$, n = 1 | (R)-N-Acryloyl thioproline-1-menthyl-amide (R)-sulphoxide | 127 | −127.2 | 61 |
| 27 | R = F, R$_1$ = H, R$_1$ = CH$_3$<br>R$_3$ = (1S)-bornyl, X = O<br>A = CH$_2$CH$_2$, n = 1 | N-Fluoroacryloyl L-methionine (1S)-bornyl ester (R,S)-sulphoxide | oil | +2.0 | 52 |
| 28 | As for 27<br>but: n = 2 | N-Fluoroacryloyl L-methionine (1S)-bornyl ester sulphone | 101 | +11.5 | 80 |
| 29 | R = CH$_3$, R$_1$ = H, R$_2$ = CH$_3$<br>R$_3$ = tert.-butyl, X = O<br>A = CH$_2$CH$_2$, n = 2 | N-Methacryloyl-L-methionine tert.-butyl ester sulphone | 99 | +25.3 | 79 |
| 30 | R = H, R$_1$ = H, R$_2$ = CH$_3$<br>R$_3$ = (1S)-bornyl, X = O<br>A = CH$_2$CH$_2$, n = 2 | N-Acryloyl L-methionine (1S)-bornyl ester sulphone | oil | +3.8 | 78 |
| 31 | As for 30<br>but R = CH$_3$ | N-Methacryloyl-L-methionine (1S)-bornyl ester sulphone | 110 | −6.6 | 69 |
| 32 | R = H, R$_2$R$_1$ = CH$_2$<br>R$_3$ = 3,5-dimethylphenyl<br>X = NH, A = CH$_2$, n = 1 | (R)-N-Acryloyl-thio-proline-3,5-dimethyl-anilide (R)-sulphoxide | 204 | −240.9 | 52 |
| 33 | R = CH$_3$, R$_1$ = H, R$_2$ = CH$_3$<br>R$_3$ = (S)-phenylethyl<br>X = NH, A = CH$_2$CH$_2$, n = 2 | N-Methacryloyl-L-methionine-(S)-phenylethylamide sulphone | 125 | −117.7 | 74 |
| 34 | R = CH$_3$, R$_1$ = H, R$_2$ = CH$_3$<br>R$_3$ = phenyl, X = NH<br>A = CH$_2$CH$_2$, n = 2 | N-Methacryloyl-L-methionine-phenylamide sulphone | 137 | −20.3 | 83 |
| 35 | R = CH$_3$, R$_1$ = H, R$_2$ = CH$_3$<br>R$_3$ = 3-pentyl, X = NH<br>A = CH$_2$CH$_2$, n = 2 | N-Methacryloyl-L-methionine-3-pentyl-amide sulphone | 134 | +8.6 (MeOH) | 94 |
| 36 | R = CH$_3$, R$_1$ = H, R$_2$ = CH$_3$<br>R$_3$ = ethyl, X = NEt<br>A = CH$_2$, n = 2 | N-Methacryloyl-S-methyl-L-cysteine-diethylamide sulphone | oil | −21.1 | 65 |
| 37 | R = CH$_3$, R$_1$ = H, R$_2$ = CH$_3$<br>R$_3$ = 1-menthyl, X = O<br>A = CH$_2$, n = 2 | N-Methacryloyl-S-methyl-L-cysteine 1-menthyl ester sulphone | 128 | −39.8 | 56 |
| 38 | As for 37<br>but: n = 1 | N-Methacryloyl-S-methyl-L-cysteine 1-menthyl ester (R,S)-sulphoxide | 120 | −46.8 | 59 |
| 39 | R = CH$_3$, R$_1$ = H, R$_2$ = CH$_2$Ph<br>R$_3$ = 1-menthyl, X = NH<br>A = CH$_2$, n = 2 | N-Methacryloyl-S-benzyl-L-cysteine-1-menthylamide sulphone | 185 | −34.0 | 69 |
| 40 | R = CH$_3$, R$_1$ = H, R$_2$ = CH$_2$Ph<br>R$_3$ = 1-menthyl, X = NH<br>A = CH$_2$, n = 1 | N-Methacryloyl-S-benzyl-L-cysteinie-1-menthylamide (R,S)-sulphoxide | 203–205 | −49.9 | 85 |
| 41 | R = CH$_3$, R$_1$ = H, R$_2$ = CH$_3$<br>R$_3$ = 3-pentyl, X = NH | N-Methacryloyl-S-methyl-L-cysteine- | 152 | −51.9 | 96 |

TABLE 1-continued

Synthesis of monomers

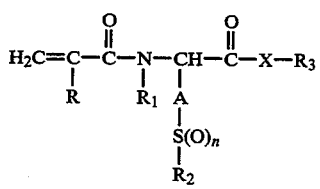

| Example | Radical groups | Product name | m.p. (°C.) | $[\alpha]_D$ (c = 1, CHCl$_3$) | Yield (%) |
|---|---|---|---|---|---|
|  | A = CH$_2$, n = 1 |  2-pentylamide (R,S)-sulphoxide |  |  |  |
| 42 | R = CH$_3$, R$_1$ = H, R$_2$ = CH$_3$ R$_3$ = 3-pentyl, X = NH A = CH$_2$, n = 2 | N-Methacryloyl-S-methyl-L-cysteine-3-pentylamide sulphone | 144 | −34.0 | 57 |
| 43 | R = CH$_3$, R$_1$ = H, R$_2$ = CH$_3$ R$_3$ = (S)-phenylethyl X = NH, A = CH$_2$, n = 1 | N-Methacryloyl-S-methyl-L-cysteine-(S)-phenylethylamide (R,S)-sulphoxide | 161 | −80.8 | 91 |
| 44 | R = CH$_3$, R$_1$ = H, R$_2$ = CH$_3$ R$_3$ = 3-methylenyl-pinanyl X = NH, A = CH$_2$ n = 1 | N-Methacryloyl-S-methyl-L-cysteine-3-(3S)-pinanylmethyl-amide (R,S)-sulphoxide | 123–125 | −20,8 | 64 |
| 45 | R = CH$_3$, R$_1$ = H, R$_2$ = CH$_3$ R$_3$ = (R)-phenylethyl X = NH, A = CH$_2$, n = 1 | N-Methacryloyl-S-methyl-L-cysteine-(R)-phenyl-ethylamide (R,S)-sulphoxide | 164–165 | −41,9 | 74 |
| 46 | R = CH$_3$, R$_1$ = H, R$_2$ = CH$_3$ R$_3$ = d-neomenthyl X = NH, A = CH$_2$, n = 1 | N-Methacryloyl-S-methyl-L-cysteine-d-neomenthyl-amide (R,S)-sulphoxide | 138–140 | −27,1 | 55 |

3) Polymerisation of the Optically active S-oxides-containing Amino acid Derivatives of the Formula I on Silica Gel a) Preparation of vinyl silica 600 ml of dry toluene are added to 50 g of silica gel (LiCHrosorb Si 100, 5μ, Merck; Polygosil 100-5, Machery & Nagel) dried at 120° C. with rigorous exclusion of moisture. 100 ml of toluene are distilled off at atmospheric pressure under N$_2$.

After cooling to 30° C., 35 g of trichlorovinylsilane are added. The batch is heated to reflux with stirring (precision glass stirrer). 62 g of dry ethylamine in 150 ml of toluene are added dropwise over a period of one hour. Stirring at 105°–108° C. is continued overnight.

After cooling, the silica gel is filtered off with suction through a sintered glass crucible, stirred in succession in toluene, dichloromethane, methanol, methanol/water=60/40, twice in methanol and twice in dichloromethane, filtered off with suction between each treatment until thoroughly dry and finally dried at 70° C.

Analyses: C: 2.8–3.2%; H: 0.7–0.9% b) Preparation of the chiral silica gels 3.0 g of vinylsilica, 2.0 g of monomer (see Table 2) and 40 mg of azobisisobutyronitrile are dissolved or suspended in 8 ml of toluene, toluene/heptane mixture or chloroform. The apparatus is evacuated three times with magnetic stirring and aerated with nitrogen. The mixture is stirred at room temperature for 1 hour, then rapidly heated to 80° C. (or 55° C. in the case of chloroform) and left at this temperature for 45 minutes. After addition of 100 mg of 2,6-di-tert.-butyl-4-methylphenol, the mixture is rapidly cooled to room temperature. The silica gel is filtered off with suction through a G4 sintered glass crucible, stirred twice in chloroform, once in toluene and once in isopropanol for 15 minutes each time, filtered off with suction until thoroughly dry and dried at room temperature in vacuo (<0.005 atm).

Yield: 3.35 g±10%

Degree of coverage, see Table 2.

TABLE 2

| | Silica gel phases | | | |
|---|---|---|---|---|
| Example | Monomer | Solvent | N content [%] | Bound polymer [% by wt.] |
| 1A | 1e | CHCl$_3$ | 1.0 | 13.2 |
| 2A | 2 | CHCl$_3$ | 1.2 | 15.9 |
| 3A | 3c | toluene | 0.7 | 18.6 |
| 4A | 4 | toluene | 0.55 | 15.2 |
| 5A | 5d | CHCl$_3$ | 0.75 | 9.9 |
| 6A | 6 | toluene | 1.2 | 16.6 |
| 7A | 7c | CHCl$_3$ | 0.8 | 10.7 |
| 8A | 8 | CHCl$_3$ | 0.7 | 8.9 |
| 9A | 9 | CHCl$_3$ | 0.5 | 12.8 |
| 10A | 10 | toluene | 1.3 | 16.6 |
| 11A | 11 | CHCl$_3$ | 0.55 | 14.0 |
| 12A | 12 | toluene | 0.65 | 17.3 |
| 13A | 13 | toluene | 1.5 | 19.9 |
| 14A | 14 | toluene | 1.2 | 15.3 |
| 15A | 15 | CHCl$_3$ | 1.05 | 14.0 |
| 16A | 16 | CHCl$_3$ | 0.35 | 9.3 |
| 17A | 17 | CHCl$_3$ | 0.6 | 16.0 |
| 18A | 18 | toluene | 1.55 | 20.6 |
| 19A | 19 | toluene | 0.8 | 11.0 |
| 20A | 20 | toluene | 0.75 | 20.8 |
| 21A | 21 | toluene | 0.7 | 8.5 |
| 22A | 22 | toluene | 0.5 | 12.2 |
| 23A | 23 | toluene | 1.25 | 23.5 |
| 24A | 24c | toluene | 0.65 | 15.9 |
| 25A | 25c | toluene | 0.6 | 14.6 |
| 27A | 27 | toluene | 0.6 | 16.0 |
| 28A | 28 | toluene | 0.5 | 13.9 |
| 29A | 29 | toluene | 1.3 | 28.3 |
| 30A | 30 | toluene | 0.65 | 17.3 |
| 31A | 31 | CHCl$_3$ | 0.4 | 11.0 |
| 32A | 32 | CHCl$_3$ | 0.9 | 9.8 |
| 33A | 33 | CHCl$_3$ | 1.25 | 15.7 |
| 34A | 34 | CHCl$_3$ | 1.7 | 19.7 |
| 35A | 35 | CHCl$_3$ | 2.0 | 22.8 |
| 36A | 36 | toluene/ heptane (containing 0.5 g of | 1.2 | 12.4 |

TABLE 2-continued

Silica gel phases

| Example | Monomer | Solvent | N content [%] | Bound polymer [% by wt.] |
|---|---|---|---|---|
| | | monomer 36) | | |
| 37A | 37 | toluene | 0.3 | 8.0 |
| 38A | 38 | toluene | 0.45 | 11.5 |
| 39A | 39 | CHCl$_3$ | 0.85 | 13.6 |
| 40A | 40 | CHCl$_3$ | 0.75 | 11.6 |
| 41A | 41 | CHCl$_3$ | 1.9 | 19.6 |
| 42A | 42 | CHCl$_3$ | 1.6 | 17.4 |

4) Polymerisation of the Optically Active S-oxides Containing Amino Acid Derivatives of the Formula (I) to give Bead Polymers

EXAMPLE 7B 13.0 g of N-methacryloyl-S-methyl-L-cysteine-1-menthylamide sulphone (see monomer 7c)), 2.0 g of N,N′,N″-tris(acryloyl)perhydrotriazine) (triacrylformal), 0.5 g of azobisisobutyronitrile, 45 g of trichloromethane and a solution of 4 g of polyvinyl alcohol in 130 ml of 1M phosphate buffer of pH 6.0 are introduced into a 250 ml stirred apparatus. The apparatus is evacuated several times and again filled with nitrogen. The mixture is then stirred at 425 rpm under nitrogen and polymerised at 45° C. for 15 minutes, at 50° C. for 30 minutes and at 55° C. for 14 hours. The fines <10 μm are separated off by repeated sedimentation in water, the beads are filtered off with suction, washed thoroughly with acetone, trichloromethane and again with acetone and dried at 50° C.

Yield: 13 g of bead polymers
Particle size: 10–40 μm
Bulk volume: 2.0 ml/g
Swelling volume: 4.5 ml/g (in toluene/THF=3/2 (v/v))

TABLE 3

Bead polymers

| Example | Monomer | Crosslinking agent | Particle size | Vb [ml/g] | Vs [ml/g] |
|---|---|---|---|---|---|
| 7B | 7c | 13.3% tri-acrylformal | 10–40 | 2.0 | 4.5 |
| 8B | 8 | 13.3% tri-acrylformal | 10–80 | 1.7 | 4.7 |

5) Use of the Optically Active Polymers of the S-oxides-containing Amino Acid Derivatives I as Adsorbents for Resolution of Racemates For the chromatographic separations, the following test racemates were used:
Racemate No. 1: binaphthol
Racemate No. 2: chlorothalidone
Racemate No. 3: mandelamide
Racemate No. 4: ibuprofenamide
Racemate No. 5: trifluoroanthrylethanol
Racemate No. 6: benzoin
Racemate No. 7: thiaprofenic acid The polymers bound to silica gel were used in steel columns (inner diameter: 4 mm; length: 25 cm) under HPLC conditions. The products were eluted using n-heptane/tetrahydrofuran mixtures (e.g. 1:1 and 1:4 (vol/vol) or n-heptane/isopropanol mixtures (e.g.: 10:1 (vol/vol)). The eluent flow rate was 1 ml/min.

The bead polymers were used in a glass column (inner diameter: 1.2 cm; bed height: 25–30 cm) under low-pressure conditions. The products were eluted using a toluene/tetrahydrofuran mixture=3:1 (vol/vol). The eluent flow rate was 0.5 ml/min.

The results obtained in chromatographic separation of the various test racemates (enantioselectivity α and capacity ratio k$_1$′) and the eluents used are summarised in Tables 4 and 5. Table 4 gives two examples of the adsorbent according to the invention (n=1 and n=2 in the monomer formula I) and compares them with the analogous phase where n is 0 (monomer formula I). It can be seen that the S-oxide phases are not only superior to the sulphide phases in respect of enantioselectivity α but, very surprisingly, also operate by a different separation mechanism, as is evident from the reversal of the order of eluent of the enantiomers of test racemate No. 2 and No. 3 ((−) before (+) means that the (−)-rotary enantiomer is eluted before the (+)-rotary enantiomer (polarimeter)).

TABLE 4

Separation results for monomer Example 7c (n = 2) and 8 (n = 1) (HPLC)

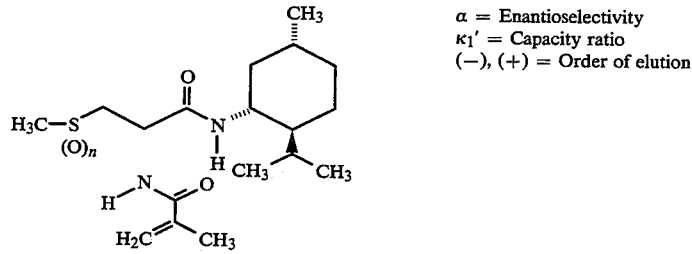

α = Enantioselectivity
κ$_1$′ = Capacity ratio
(−), (+) = Order of elution

| Racemate | n = 0 (sulphide) | n = 1 (sulphoxide) | n = 2 (sulphone) | Eluant |
|---|---|---|---|---|
| No. 1 | α = 1.23<br>κ$_1$′ = 0.47 | α = 2.28<br>κ$_1$′ = 1.08 | α = 2.46<br>κ$_1$′ = 0.40 | n-heptane:<br>THF = 1:1 |
| No. 2 | α = 1.84<br>κ$_1$′ = 0.47<br>(+) before (−) | α = 4.59<br>κ$_1$′ = 1.08<br>(−) before (+) | α = 3.80<br>κ$_1$′ = 0.30<br>(−) before (+) | n-heptane:<br>THF = 1:4 |
| No. 3 | α = 1.23<br>κ$_1$′ = 0.95<br>(+) before (−) | α = 2.57<br>κ$_1$′ = 0.64<br>(−) before (+) | α = 1.78<br>κ$_1$′ = 0.62<br>(−) before (+) | n-heptane:<br>THF = 1:4 |

TABLE 4-continued

Separation results for monomer Example 7c (n = 2) and 8 (n = 1) (HPLC)

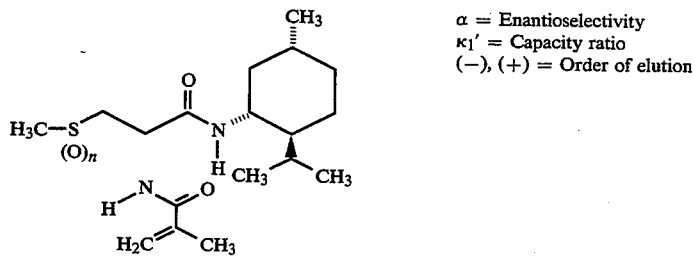

α = Enantioselectivity
κ₁' = Capacity ratio
(−), (+) = Order of elution

| Racemate | n = 0 (sulphide) | n = 1 (sulphoxide) | n = 2 (sulphone) | Eluant |
|---|---|---|---|---|
| No. 4 | α = 1.38 | α = 1.88 | α = 1.54 | n-heptane: |
|  | κ₁' = 1.62 | κ₁' = 1.14 | κ₁' = 0.93 | THF = 1:1 |
| No. 5 | α = 1.00 | α = 1.20 | α = 1.09 | n-heptane: |
|  | no separation | κ₁' = 1.73 | κ₁' = 1.01 | isopropanol = 10:1 |
| No. 6 | α = 1.00 | α = 1.00 | α = 1.56 | n-heptane: |
|  | no separation | no separation | κ₁' = 1.20 | isopropanol = 10:1 |
| No. 7 | α = 1.00 | α = 1.37 | α = 1.00 | n-heptane: |
|  | no separation | κ₁' = 0.80 | no separation | THF = 1:1 |
|  |  | (+) before (−) |  |  |

TABLE 5

Separation results for monomer Example 40 (n = 1)

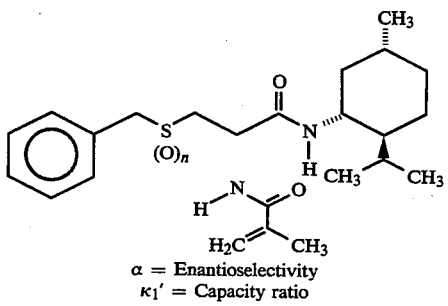

α = Enantioselectivity
κ₁' = Capacity ratio

| Racemate | n = 0 (sulphide) | n = 1 (sulphoxide) | Eluent |
|---|---|---|---|
| No. 1 | α = 1.00 (no separation) | α = 1,79 κ₁' = 1.09 | n-heptane: THF = 1:1 |
| No. 2 | α = 1.00 (no separation) | α = 5,82 κ₁' = 0.39 | n-heptane: THF = 1:4 |
| No. 3 | α = 1.25 κ₁' = 0.44 | α = 3,30 κ₁' = 1.62 | n-heptane: THF = 1:4 |
| No. 5 | α = 1.10 κ₁' = 0.71 | α = 1,18 κ₁' = 1.67 | n-heptane: isopropanol = 10:1 |
| No. 6 | α = 1.00 (no separation) | α = 1,24 κ₁' = 0.98 | n-heptane: isopropanol = 10:1 |
| No. 7 | α = 1.00 (no separation) | α = 1.48 κ₁ = 0.85 (+) before (−) | n-heptane: THF = 1:1 |

We claim:

1. An optically pure crosslinked insoluble polymer containing at least 40 mol % of structural units of the formula

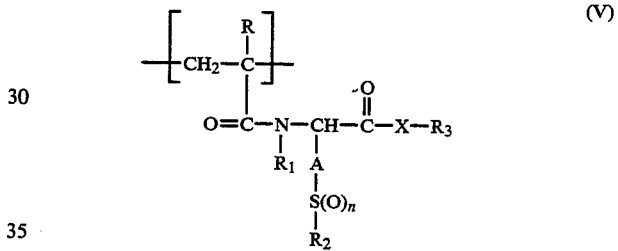

in which n is 1 or 2,

R represents hydrogen, methyl or fluorine, $R_1$ represents hydrogen or $C_1$-$C_4$-alkyl or together with $R_2$ forms a methylene group or a dimethylene group, each of which can be mono- or disubstituted by $C_1$-$C_4$-alkyl, $R_2$ represents a straight-chain, branched or cyclic alkyl radical having up to 10 C atoms, $C_6$-$C_{14}$-aryl, $$-CH_2-\overset{O}{\underset{\|}{C}}-X-R_3,$$

$C_2$-$C_{10}$-acyl, substituted or unsubstituted benzoyl or benzyl or together with $R_1$ forms a bridge, $R_3$ represents a straight-chain, branched or cyclic alkyl radical having up to 20 C atoms which is unsubstituted or mono- to trisubstituted by halogen, alkoxy having 1 to 4 C atoms, aralkoxy having 7 to 16 C atoms or aryl having 6 to 10 C atoms, X denotes oxygen or an $NR_4$ group in which $R_4$ represents hydrogen or $C_1$-$C_4$-alkyl or together with $R_3$ forms a nitrogen-containing 5- to 7-membered ring which may be mono- or disubstituted by $C_1$-$C_4$-alkyl- or $C_1$-$C_6$-alkoxycarbonyl, and A represents a methylene or dimethylene group which is unsubstituted or mono- or disubstituted by $C_1$-$C_4$-alkyl.

2. A polymer according to claim 1, in which
R represents hydrogen, methyl or fluorine, $R_1$ denotes hydrogen or methyl or together with $R_2$ forms a methylene group, which can be mono- or disubstituted by methyl or monosubstituted by tertiary-butyl, or a dimethylene group, $R_2$ represents alkyl having up to 8 C atoms, phenyl, benzyl, benzoyl and

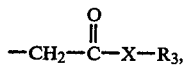

or together with $R_1$ forms a bridge, $R_3$ represents a $C_{10}$-terpenyl radical, an adamantyl radical, a decahydronaphthyl radical, a 1-phenylethyl radical, a $C_5$-$C_{12}$-cycloalkyl radical, such as cyclopentyl, cyclohexyl or cycloheptyl, or a branched $C_3$-$C_{12}$-alkyl radical, such as isopropyl, 3-pentyl or 5-heptyl, X denotes oxygen or an $NR_4$ group in which $R_4$ represents hydrogen or $C_1$-$C_4$-alkyl or together with $R_3$ forms a nitrogen-containing 5- to 7-membered ring which may be unsubstituted or mono- or disubstituted by $C_1$-$C_4$-alkyl- or $C_1$-$C_6$-alkoxycarbonyl, and A represents a methylene, dimethylmethylne or dimethylene unit.

3. A polymer according to claim 1, containing the amino acid sequence of the optically active sulphur-containing amino acids, cysteine, homocysteine, penicillamine whose SH function is first alkylated, arylated, alkoxycarbonylmethylated or linked to the amino group via an alkylene bridge and secondly has been oxidized to the sulphoxide or sulphone.

4. A polymer according to claim 1, in the form of beads or bound to a finely divided inorganic support.

5. A process for the preparation of a crosslinked bead polymer according to claim 1, which comprises polymerizing an optically active S-oxide-containing amino acid of the formula

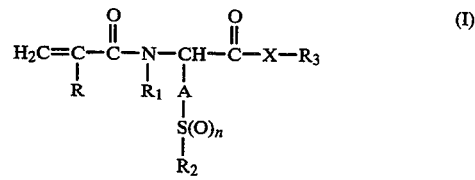

in suspension in the presence of 0.5 to 50 mol % of a crosslinking agent.

6. A process according to claim 5, wherein the polymerization is effected in the presence of at least one of a free radical former and an inert organic solvent.

7. A process for the preparation of a crosslinked polymer according to claim 1 bound to an inorganic support material, which comprises polymerizing an optically active S-oxide-containing amino acid of the formula

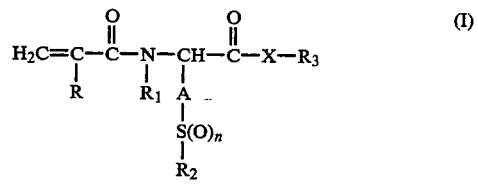

in the presence of a (meth)acryloyl-substituted silica gel/diol phase or a silica gel/vinyl phase.

8. A process according to claim 7, wherein the polymerization is effected in the presence of at least one of a free radical former and an inert organic solvent.

9. In the resolution of a racemic mixture of a compound into its optical antipodes by contacting such mixture with an optically active adsorbent, the improvement wherein such adsorbent comprises a polymer according to claim 1.

* * * * *